United States Patent
Dobashi et al.

(10) Patent No.: US 8,268,185 B2
(45) Date of Patent: Sep. 18, 2012

(54) METHOD FOR ANALYZING QUARTZ MEMBER

(75) Inventors: Kazuya Dobashi, Nirasaki (JP); Teruyuki Hayashi, Nirasaki (JP); Kohei Tsugita, Nirasaki (JP); Misako Saito, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 839 days.

(21) Appl. No.: 12/097,767

(22) PCT Filed: May 28, 2007

(86) PCT No.: PCT/JP2007/060791
§ 371 (c)(1),
(2), (4) Date: Jun. 17, 2008

(87) PCT Pub. No.: WO2007/142058
PCT Pub. Date: Dec. 13, 2007

(65) Prior Publication Data
US 2008/0302762 A1    Dec. 11, 2008

(30) Foreign Application Priority Data

Jun. 2, 2006  (JP) .................................. 2006-154988

(51) Int. Cl.
*G01N 1/32* (2006.01)
*G01N 1/28* (2006.01)

(52) U.S. Cl. ................................. 216/97; 216/83; 216/84

(58) Field of Classification Search ................... 216/84, 216/83, 97
See application file for complete search history.

(56) References Cited

U.S. PATENT DOCUMENTS 5,445,708 A * 8/1995 Ishii ............................... 216/17

FOREIGN PATENT DOCUMENTS

| JP | 8 148536 | 6/1996 |
|---|---|---|
| JP | 08148536 A * | 6/1996 |
| JP | 11 204603 | 7/1999 |
| JP | 11204603 A * | 7/1999 |
| JP | 2000 97822 | 4/2000 |
| JP | 2001 223251 | 8/2001 |
| JP | 2001223251 A * | 8/2001 |
| JP | 2003 17538 | 1/2003 |
| JP | 2004 69502 | 3/2004 |
| JP | 2004069502 A * | 3/2004 |
| JP | 2005 114582 | 4/2005 |

* cited by examiner

*Primary Examiner* — Lan Vinh
*Assistant Examiner* — David Kaufman
(74) *Attorney, Agent, or Firm* — Oblon, Spivak, McClelland, Maier & Neustadt, L.L.P.

(57) ABSTRACT

A method of analyzing a quartz member includes the step of supplying an etchant to the quartz member so as to etch the quartz member. The method also includes analyzing the etchant used in the supplying step. The etchant is supplied to a concave etchant receiving portion that is formed in the quartz member prior to the supplying step and has an inner wall thereof formed of the quartz member.

8 Claims, 6 Drawing Sheets

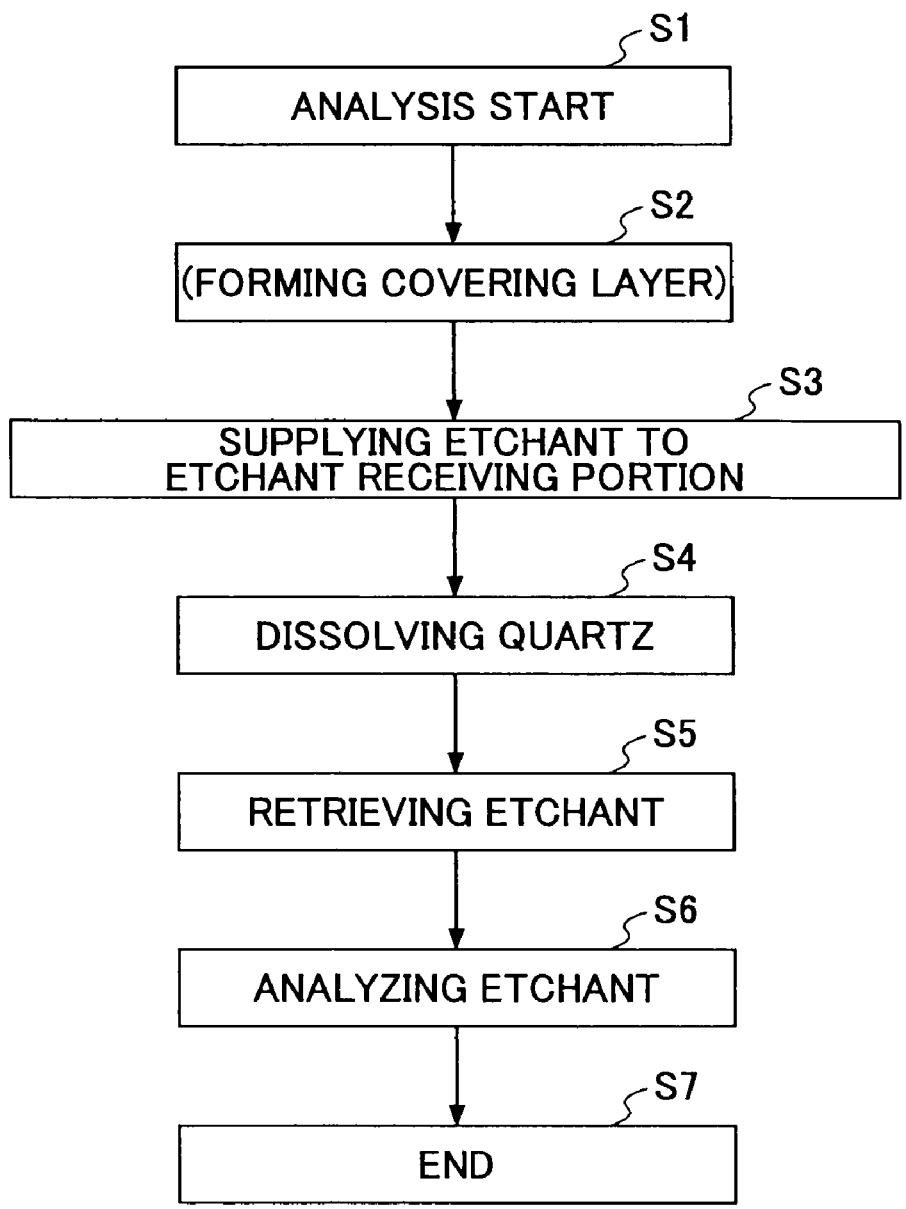

METHOD FOR ANALYZING QUARTZ MEMBER

CROSS REFERENCE TO RELATED APPLICATIONS

This application claims priority under 35 U.S.C. 119(a) to Japanese Patent Application No. 2006-154988 filed Jun. 2, 2006, the entire contents of which is incorporated herein by reference.

TECHNICAL FIELD

This invention relates to a method of analyzing quartz members, specifically to a method of analyzing contamination in the quartz members.

BACKGROUND ART

Quartz members have been widely used in various substrate processing apparatuses, for example, for fabricating semiconductor devices, because quartz has a high melting point and less degassing under a reduced atmosphere environment. In addition, the quartz members may have less adverse effect as a source of contamination on semiconductor devices such as highly sophisticated devices. Therefore, the quartz members are preferable for the substrate processing apparatuses, which require a strict control of contamination.

However, even when quartz material to be used for making the quartz members is highly purified, the quartz material may be contaminated, for example, when the material is machined into the quartz members. If the quartz members contaminated during machining are used in the substrate processing apparatus for fabricating the semiconductor devices, semiconductor wafers may also be contaminated, thereby reducing the production yield of the semiconductor devices.

In order to address such a disadvantage, various methods have been proposed to detect metal contamination in the quartz members. One of the examples of such methods is to detect (analyze) metal contamination of the quartz members by immersing the quartz members into an etchant which in turn is analyzed (see Patent Document 1 listed below).

Patent Document 1: Japanese Laid-Open Patent Application No. 2001-223251.

DISCLOSURE OF THE INVENTION

Problems to be Solved by the Invention

However, since immersing the quartz members in a predetermined etchant requires a container to be full of the etchant, if the container itself is contaminated, there is caused a disadvantage of reduced detection accuracy of contamination.

In addition, when the quartz members to be subjected to the contamination analysis are large, the container to hold the etchant has to be also large and thus the etchant touches a larger area of the inner surface of the container. In this case, various substances may be dissolved into the etchant from the inner surface of the container, which may have an adverse effect on the measurement.

Moreover, when the quartz members are large, not only the container has to be large but also a larger amount of the etchant is required, which leads to an increased analysis cost. Furthermore, handling a large amount of the etchant requires extreme caution. For example, when strong acid such as hydrofluoric acid is used as the etchant, increased safety management costs are inevitable.

On the other hand, there is an analysis method, such as method employing secondary ion mass spectrometry (SIMS), which does not require the etchant. However, such a method is limited in terms of detectable depth and thus disadvantageous in that sufficient analysis cannot be carried out. In addition, there is also a method of optically analyzing the quartz members. However, this method is disadvantageous in that destructive inspection is required.

The present invention has been made in view of above, and is directed to a method of enabling simple but accurate analysis of the quartz members.

Means of Solving the Problems

A first aspect of the present invention provides a method of analyzing a quartz member. This method includes steps of supplying an etchant to an etchant receiving portion formed concavely in the quartz member so as to etch the quartz member; and analyzing the etchant used in the supplying step.

In a second aspect of the present invention, the etchant receiving portion includes an opening with a curved line in the method of analyzing the quartz member according to the first aspect.

In a third aspect of the present invention, the etchant receiving portion may be substantially tubular shaped in the method of analyzing the quartz member according to the first or the second aspect.

In a fourth aspect of the present invention, a covering layer that prevents the etchant from flowing out from the etchant receiving portion may be formed around the etchant receiving portion in the method of analyzing the quartz member according to any one of the first through the third aspects.

In a fifth aspect of the present invention, the covering layer may be formed of an organic material in the method of analyzing the quartz member according to the fourth aspect.

In a sixth aspect of the present invention, the etchant may include hydrofluoric acid in the method of analyzing the quartz member according to any one of the first through the fifth aspects.

In a seventh aspect of the present invention, the etchant may be analyzed by either one of inductively-coupled plasma source mass spectrometry, inductively-coupled plasma atomic emission spectrometry, and atomic absorption spectrometry in the analyzing step, in the method of analyzing the quartz member according to any one of the first through the sixth aspects.

In an eighth aspect of the present invention, the quartz member may be used in a substrate processing apparatus for use in production of semiconductor devices, in the method of analyzing the quartz member according to any one of the first through the seventh aspects.

EFFECTS OF THE INVENTION

According to the present invention, a method of enabling simple but accurate analysis of quartz members can be provided.

BRIEF DESCRIPTION OF THE DRAWING

FIG. 8 is a flowchart of a method of analyzing a quartz member, according to an embodiment of the present invention.

Figure 1A:
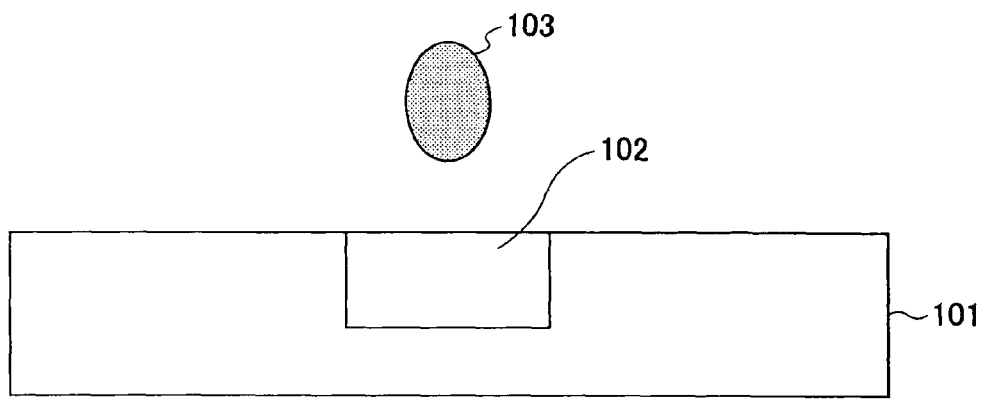
FIG. 1A is a schematic view illustrating a step of a method of analyzing a quartz member.

DESCRIPTION OF THE REFERENCE NUMERALS 101 quartz member
102, 102A, 102B, 102C, 102D etchant receiving portion
103 etchant
104 covering layer

BEST MODE OF CARRYING OUT THE INVENTION

Referring to the accompanying drawings, embodiments of the present invention will be described. In the drawings, the same or corresponding reference marks are given to the same or corresponding members or components.

Figure 1B:
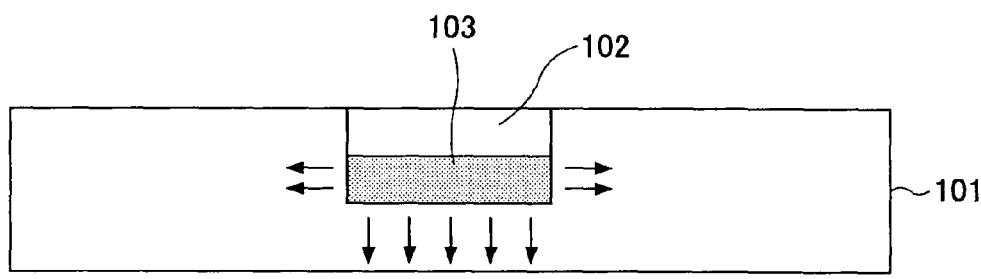
FIG. 1B is a schematic view illustrating another step of the method of analyzing the quartz member.

FIGS. 1A and 1B are schematic views illustrating a method of analyzing quartz members, according to an embodiment of the present invention. As shown in FIG. 1A, an etchant 103 is supplied (dispensed) on a quartz member 101. In the analysis method according to this embodiment, a concave etchant receiving portion 102 is formed in an area of the quartz member 101 where the etchant 103 is dispensed.

The etchant 103 used in this embodiment may preferably include, for example, a hydrofluoric acid-containing solution and a mixture of hydrofluoric acid and nitric acid, hydrochloric acid, sulfuric acid, hydrogen peroxide, or the like.

The etchant receiving portion 102 may be formed in an area to be subjected to the analysis at the time of producing the quartz member 101 or before starting the analysis. By the way, the area subjected to the analysis may be an area that is expected to be heated when the quartz member 101 is used in the substrate processing apparatus, or in the vicinity of a portion where a semiconductor substrate (wafer) is placed. In addition, plural of the etchant receiving portions 102 can be formed in one quartz member 101. The etchant receiving portions 102 may be formed by etching the quartz member 101 using a mask having a predetermined opening.

As shown in FIG. 1B, the etchant 103 dispensed on the quartz member 101 remains in the etchant receiving portions 102. The etchant 103 etches the inner wall of the etchant receiving portions 102. In this embodiment, the etchant 103 dispensed on the quartz member 101 is received in the etchant receiving portions 102, and then this etchant 103 is used as a sample for a chemical analysis.

Namely, when the inner wall of the etchant receiving portion 102 is etched by the etchant 103, contaminants (metals) contained in the quartz member 101 are also dissolved into the etchant 103. Then, the etchant 103 is retrieved, and the retrieved etchant 103 is analyzed by a predetermined analysis method, so that the contaminants in the quartz member 101 (metal contamination) are detected.

The analysis method may include, for example, inductively-coupled plasma source mass spectrometry (ICP-MS), inductively-coupled plasma atomic emission spectrometry (ICP-AES), atomic absorption spectrometry (AAS), or the like.

For example, if a quartz member is immersed in an etchant and the etchant is analyzed as is carried out in the conventional analysis method, contamination in a container to hold the etchant may have an adverse effect on the measurement results and thus reduce measurement accuracy. In addition, such a conventional analysis method tends to require large-scale facilities, which leads to increased costs of analysis.

However, the method of analyzing the quartz member according to this embodiment of the present invention eliminates the need for the container to hold the etchant, which makes this analysis method free from contamination in the container, and enables simple but accurate analysis of the quartz member. In addition, according to the analysis method of this embodiment, there is no need to prepare containers of various sizes corresponding to the quartz members having various shapes and sizes, which is advantageous in cost reduction. Moreover, the analysis method according to this embodiment of the present invention requires a limited amount of the etchant, which is advantageous in further cost reduction.

Additionally, since the etchant 103 is held in the etchant receiving portion 102, the etchant 103 is prevented from flowing away, and thus sufficient etching is carried out regardless of surface conditions (a liquid-repellent property or a lyophilic property of the surface) of the quartz member 101.

If the etchant 103 is dispensed on the surface of the quartz member where the concave etchant receiving portion 102 is not formed, the surface of the quartz member 101 cannot be etched when the surface has a lyophilic property since the dispensed etchant 103 cannot stay on the surface.

However, since the etchant 103 can be held by the etchant receiving portion 102 in this embodiment of the present invention, the quartz member 101 can be sufficiently etched irrespective of whether the surface of the quartz member 101 is liquid-repellant or lyphilic (or regardless of surface energy of the surface of the quartz member 101).

In addition, the analysis method according to this embodiment is more advantageous than a conventional dry analysis method utilizing SIMS in terms of detectable depth. For example, the detectable depth of the analysis method according to this embodiment of the present invention can be several millimeters, when necessary, while the detectable depth of SIMS is as shallow as several hundreds micrometers. Moreover, since the analysis method according to this embodiment of the present invention is basically a non-destructive inspection, it is not necessary to chip the quartz member 101.

Figure 2A:
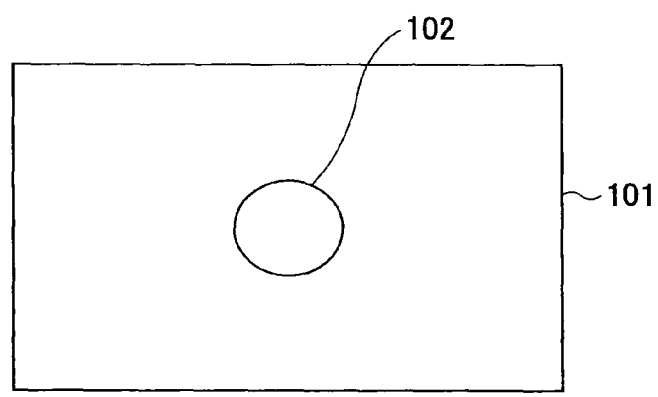
FIG. 2A is a plan view of an etchant receiving portion that is provided in the quartz member and preferable for the method of analyzing the quartz member.
Figure 2B:
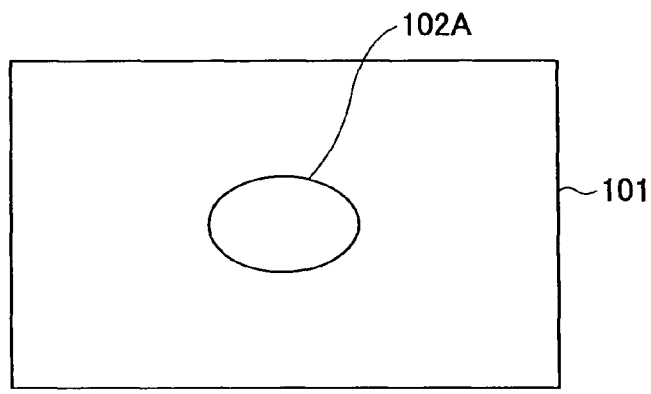
FIG. 2B is a plan view of another etchant receiving portion that is provided in the quartz member and preferable for the method of analyzing the quartz member.
Figure 2C:
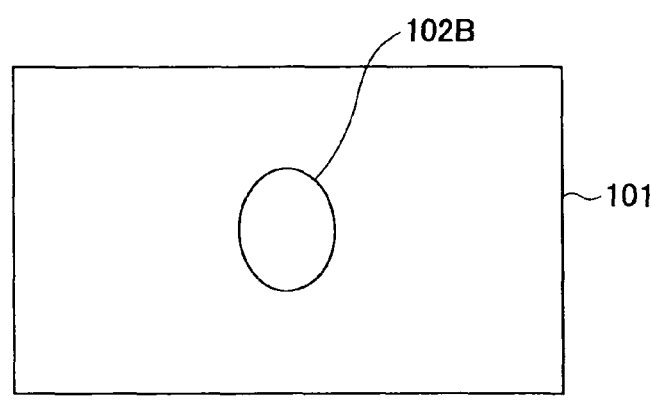
FIG. 2C is a plan view of yet another etchant receiving portion that is provided in the quartz member and preferable for the method of analyzing the quartz member.

Next, shapes of the etchant receiving portion 102 are described. FIGS. 2A through 2C are plan views illustrating the shapes of the etchant receiving portion 102 in this embodiment of the present invention.

Referring to FIG. 2A, a top-view shape of the opening of the etchant receiving portion 102 is substantially circular. In addition, as shown in FIGS. 2B and 2C, the openings of the etchant receiving portions 102A, 102B may be ellipsoidal.

As stated above, it is preferable that the opening of the etchant receiving portion be shaped with curves when seen from above. Particularly, the opening of the etchant receiving portion may more preferably be circular or ellipsoidal. This is because the etchant 103 may flow out from cornered portions if the opening includes the cornered portions. Such flowing out of the etchant 103 is described in reference to FIGS. 3 and 4.

Figure 3:
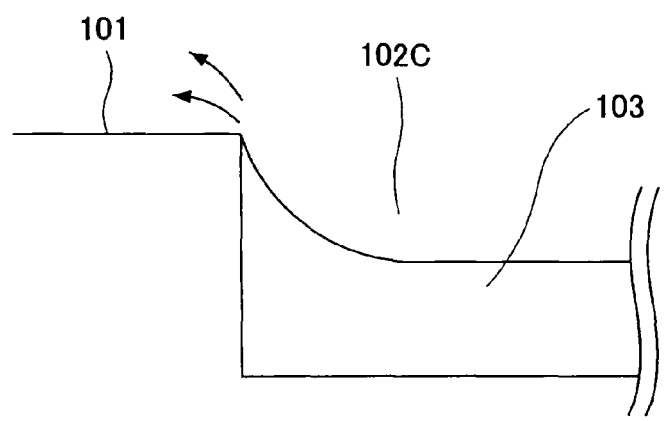
FIG. 3 is a schematic cross-sectional view of etchant held in an etchant receiving portion having a cornered portion in an opening of the etchant receiving portion.
Figure 4:
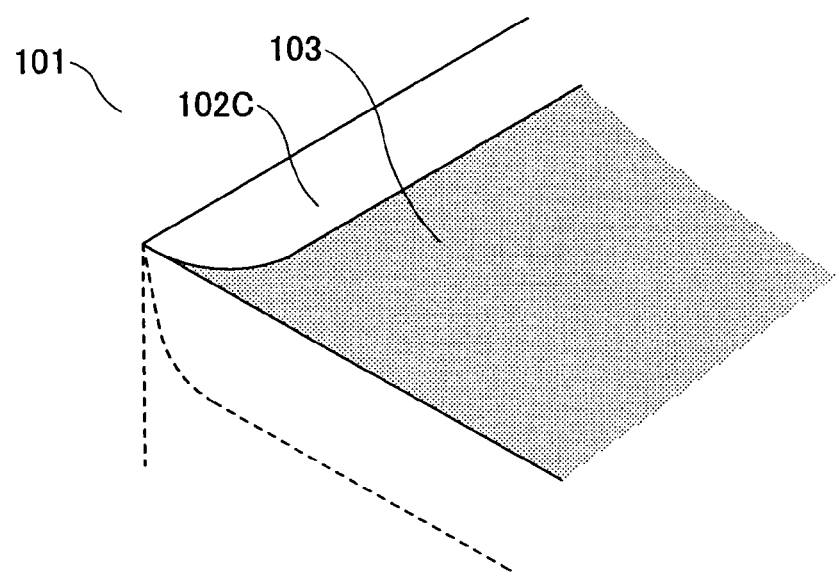
FIG. 4 is a schematic perspective view of etchant held in the etchant receiving portion having the cornered portion in the opening of the etchant receiving portion.

FIG. 3 is a cross-sectional view illustrating the etchant 103 held in an etchant receiving portion 102C whose opening includes cornered portions. FIG. 4 is a perspective view of the etchant 103 held in the etchant receiving portion 102C.

As shown in FIGS. 3 and 4, when the etchant receiving portion 102C has cornered portions, the surface of the etchant 103 in the etchant receiving portion 102C is raised toward the cornered portions. Therefore, the etchant 103 may easily flow out from the cornered portions. Such flowing out tends to occur when the etchant 103 contains acid having a low surface tension, such as hydrofluoric acid. Moreover, since such tendency becomes significant in the case of the etchant having higher concentration of hydrofluoric acid, flowing out of the etchant 103 becomes a more serious problem when increasing an etching rate with a view of increased analysis efficiency.

In this embodiment of the present invention, since the openings of the etchant receiving portions (102, 102A, 102B) have shapes including curves such as a circle or an ellipsoid (or shapes formed of curves), when seen from above, so as to exclude the cornered portions, the etchant 103 can be efficiently prevented from flowing out from the etchant receiving portion. As a result, the etchant having a high concentration of hydrofluoric acid can be used, thereby increasing the etching rate and thus improving analysis efficiency.

Figure 5A:
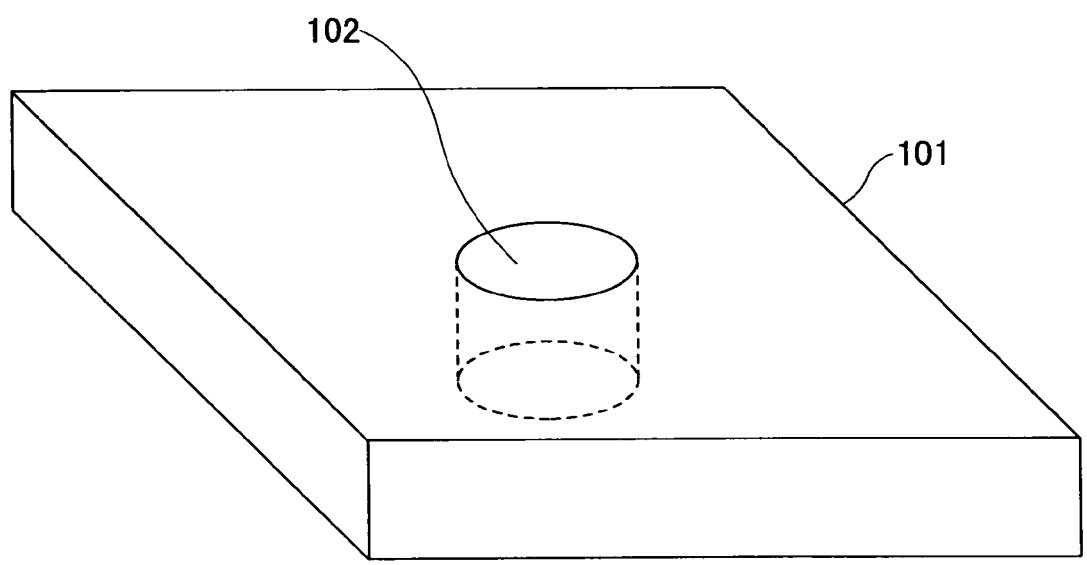
FIG. 5A shows an example of a shape of the etchant receiving portion that is provided in the quartz member and preferable for the method of analyzing the quartz member.

FIG. 5A is a perspective view of the quartz member 101. As shown in FIG. 5A, the etchant receiving portion 102 is preferably formed into, for example, a tubular shape. In this case, the etchant held by the etchant receiving portion 102 can also be effectively prevented from flowing out as described above. In addition, such a shape can be made quite easily.

Figure 5B:
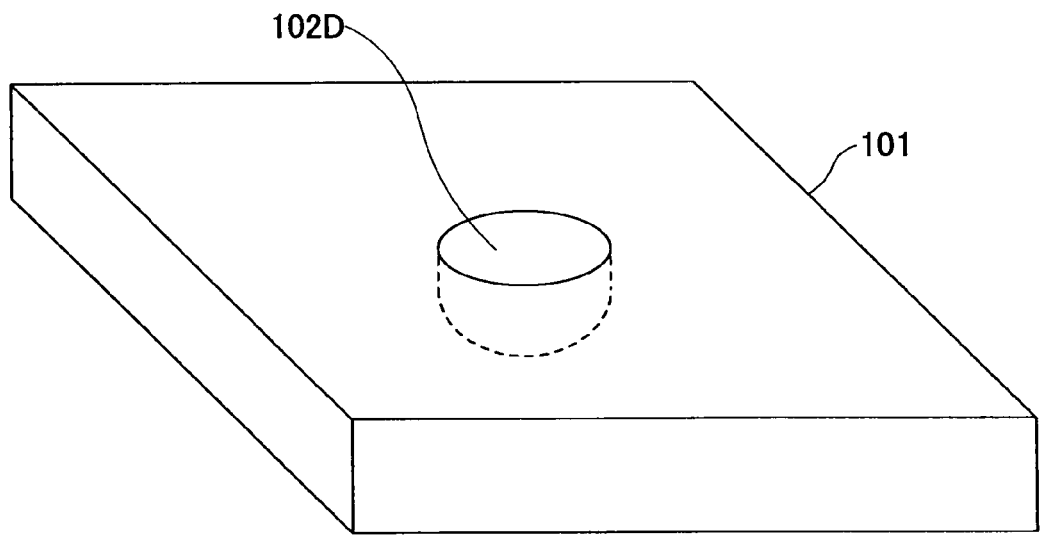
FIG. 5B shows an example of another shape of the etchant receiving portion that is provided in the quartz member and preferable for the method of analyzing the quartz member.

Moreover, the etchant receiving portion may be formed into, for example, a hemispherical shape like an etchant receiving portion 102D shown in FIG. 5B so that the inner surface of the etchant receiving portion 102D is all curved. In this case, the etchant can be more efficiently prevented from flowing out. As stated, the shapes of the etchant receiving portions may be preferably determined taking account of the preventive effect against flowing-out of the etchant and workability of the quartz member. Further, the size of the etchant receiving portion may be determined taking account of the size of the quartz member.

Figure 6A:
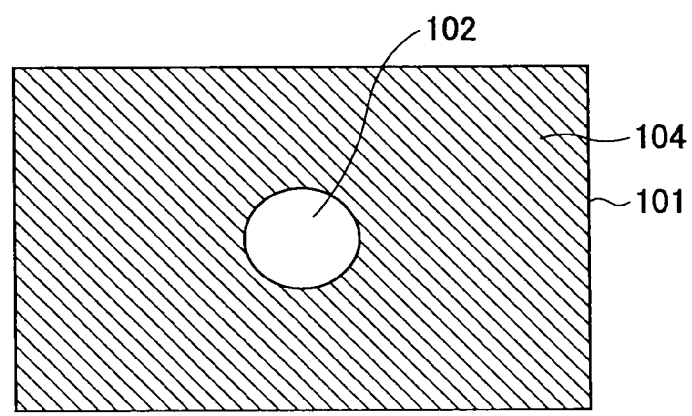
FIG. 6A shows an example of a covering layer that is formed on the quartz member and preferable for the method of analyzing the quartz member.
Figure 6B:
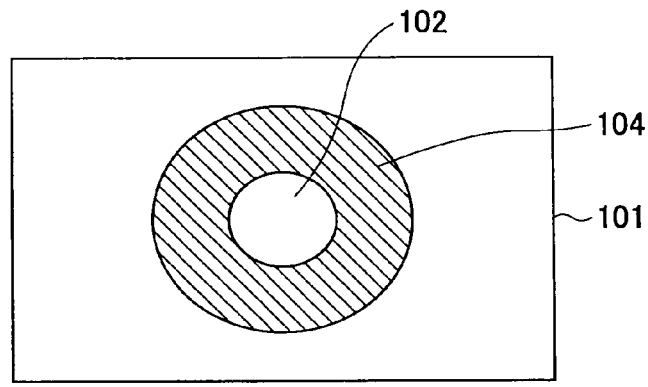
FIG. 6B shows an example of another covering layer that is formed on the quartz member and preferable for the method of analyzing the quartz member.

In order to further prevent the etchant 103 from flowing out from the etchant receiving portions 102, 102A, 102B, 102D, a predetermined covering layer is formed on an area of the quartz member 101 where the etchant receiving portion 102 (102D) is formed. FIGS. 6A and 6B are a plan view of the quartz member 101 in which the covering layer is formed around the etchant receiving portion 102.

Referring to FIG. 6A, the top surface of the quartz member 101 where the etchant receiving portion 102 is formed is covered entirely with the covering layer 104, with an exception of the inside of the etchant receiving portion 102. The covering layer 104 preferably has liquid-repellency against the etchant 103. For example, the covering layer 104 may be formed of an organic material, an example of which is dioctyly phthalate (DOP). When other organic materials are used to form the covering layer 104, the organic materials preferably have a boiling point higher than the boiling point of the DOP.

In addition, the covering layers 104 may be formed only around the etchant receiving portion (opening), as shown in FIG. 6B. In this case, the covering layer 104 is formed into, for example, a planar ring shape surrounding the etchant receiving portion 102.

Figure 7A:
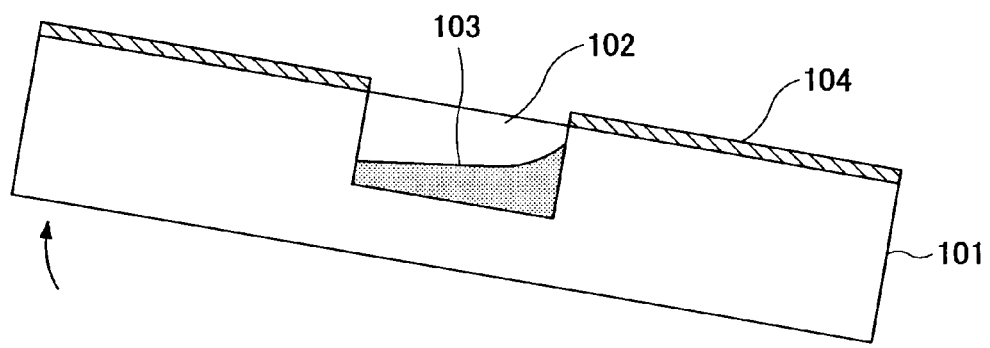
FIG. 7A is a schematic cross-sectional view of the etchant held in the etchant receiving portion around which the covering layer is formed.
Figure 7B:
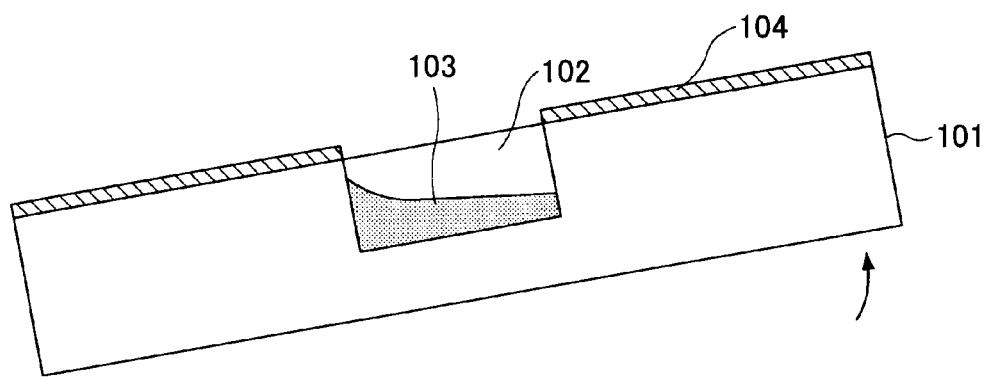
FIG. 7B is another schematic cross-sectional view of the etchant held in the etchant receiving portion around which the covering layer is formed.

When the covering layer 104 shown in FIGS. 6A and 6B are formed, the preventive effect against flowing-out of the etchant from the etchant receiving portion 102 can be further improved. FIGS. 7A and 7B are schematic cross-sectional views illustrating the etchant held in the etchant receiving portion with the covering layer 104 formed around the etchant receiving portion.

Referring to FIGS. 7A and 7B, since the covering layer 104 is formed, it becomes difficult for the etchant 103 to flow out from the etchant receiving portion 102 even when the quartz member 101 is tilted, thereby making it possible to stably hold the etchant 103 in the etchant receiving portion 102.

In addition, as shown in FIGS. 7A and 7B, when directions of tilt of the quartz member 101 are changed, the etching of the quartz member 101 is facilitated. Namely, since the etchant 103 moves in the etchant receiving portion 102, the etching rate is increased, thereby improving analysis efficiency.

By the way, the covering layer 104 may be formed by an evaporation method that deposits a source of the covering layer 104 (DOP) on the quartz member 101. However, the method of forming the covering layer 104 is not limited to the evaporation method, but various methods such as a spin-on-coating method, a screen printing method, a letterpress printing method, an engraved plate printing method, an ink-jet printing method, a sputtering method, a chemical vapor deposition method, or the like can be employed.

In addition, as a method of patterning the covering layer, there are a patterning method in which the covering layer is formed using a patterned mask, and another patterning method that employs lithography and etching.

FIG. 8 is a flowchart illustrating a method of analyzing a quartz member according to this embodiment of the present invention.

At step S1, the method according to this embodiment of the present invention is started. When necessary, the covering layer 104 described above is formed on the quartz member 101 at step S2. With this, the area surrounding the etchant receiving portion 102 is covered with an organic material (for example, DOP). However, this step may be omitted.

Next, at step S3, the etchant including, for example, hydrofluoric acid is dispensed into the etchant receiving portion 102 (FIG. 1, for example). In this case, the etchant is diluted hydrofluoric acid, or a diluted mixture of the hydrofluoric acid and nitric acid, hydrochloric acid, sulfuric acid, hydrogen peroxide, or the like.

At step S4, quartz and impurities (metal) included in the quartz are etched (dissolved) from the inner wall of the etchant receiving portion 102 by the etchant. At this step, the etchant 103 may be actively swayed as shown in FIGS. 7A and 7B so that the etching (dissolving) can be promoted.

Next, at step S5, the etchant 103 held in the etchant receiving portion 102 is retrieved.

Next, at step S6, the retrieved etchant 103 is analyzed using, for example, the ICP-MS method, the ICP-AES method, the AAS method, or the like. As a result, metal elements included in the quartz are detected. In addition, a known method (see, for example, Japanese Laid-Open Patent Application No. 2001-223251) can be used to quantitatively analyze the metal included in the quartz.

In such a manner described above, the analysis of the quartz member is completed at step S7.

According to the aforementioned method of analyzing the quartz member, the metal (metal contamination) in various quartz members for various usages can be detected (or quantitatively analyzed). Specifically, the method of analyzing the quartz member according to the embodiment of the present invention is preferably applied to analysis of the quartz member to be used for the substrate processing apparatus for fabricating semiconductor devices.

Along with recent advancements of the semiconductor devices, a stricter control of metal contamination is required in the substrate processing apparatus for fabricating the semiconductor devices. Specifically, contamination reduction in constituting members of the substrate processing apparatus has drawn considerable attention.

The quartz members are quite often used as constituting members of the substrate processing apparatus for fabricating advanced semiconductor devices since the quartz members are advantageous in terms of less degassing under a reduced pressure environment compared with other materials.

The method of analyzing the quartz according to the embodiments of the present invention enables simple but accurate analysis of the quartz member even when the quartz member is large or the shape of the quartz member is complicated.

In addition, since the method of analyzing the quartz according to the embodiment of the present invention enables non-destructive analysis, the quartz member to be used in an expensive substrate processing apparatus can be analyzed without being damaged.

The embodiment of the present invention is not limited to analysis of the quartz member for use in the substrate processing apparatus, but may be applied to the quartz members used in various fields of technology.

Although several preferred embodiments of the present invention have been explained in detail, the present invention is not limited to these embodiments, but various alterations and modifications are possible within the scope of the present invention set forth with the Claims.

INDUSTRIAL APPLICABILITY

According to the present invention, a simple but accurate analysis can be provided.

The invention claimed is:

1. A method of analyzing a quartz member, comprising steps of:
   supplying an etchant to the quartz member so as to etch the quartz member; and
   analyzing the etchant used in the supplying step; wherein
   the etchant is supplied to a concave etchant receiving portion that is formed in the quartz member prior to the supplying step and has an inner wall thereof formed of the quartz member,
   wherein the etchant is only filled below a top portion of the inner wall of the concave etchant receiving portion corresponding to a top surface of the quartz member, and
   wherein the etchant is reserved in the concave etchant receiving portion while the etchant etches the inner wall of the concave etchant receiving portion.

2. The method of analyzing the quartz member of claim 1, wherein the etchant receiving portion has an opening with a curved line.

3. The method of analyzing the quartz member of claim 1, wherein the etchant receiving portion is substantially tubular shaped.

4. The method of analyzing the quartz member of claim 1, wherein a covering layer that prevents the etchant from flowing out from the etchant receiving portion is formed around the etchant receiving portion.

5. The method of analyzing the quartz member of claim 4, wherein the covering layer is formed of an organic material.

6. The method of analyzing the quartz member of claim 1, wherein the etchant is analyzed by either one of inductively-coupled plasma source mass spectrometry, inductively-coupled plasma atomic emission spectrometry, and atomic absorption spectrometry in the analyzing step.

7. The method of analyzing the quartz member of claim 1, wherein the quartz member is to be used in a substrate processing apparatus for use in production of semiconductor devices.

8. The method of analyzing the quartz member of claim 1, wherein the supplied etchant etches the inner wall in the supplying step.

* * * * *